United States Patent
Murphy et al.

(10) Patent No.: US 12,369,844 B2
(45) Date of Patent: Jul. 29, 2025

(54) SKIN INSPECTION DEVICE FOR IDENTIFYING ABNORMALITIES

(71) Applicant: Bluedrop Medical Limited, Galway (IE)

(72) Inventors: Christopher Murphy, County Mayo (IE); Gavin Corley, County Galway (IE); Simon Kiersey, Galway (IE)

(73) Assignee: BLUEDROP MEDICAL LIMITED, Galway (IE)

( * ) Notice: Subject to any disclaimer, the term of this patent is extended or adjusted under 35 U.S.C. 154(b) by 978 days.

(21) Appl. No.: 16/303,212

(22) PCT Filed: Apr. 6, 2017

(86) PCT No.: PCT/EP2017/058294
§ 371 (c)(1),
(2) Date: Nov. 20, 2018

(87) PCT Pub. No.: WO2017/202534
PCT Pub. Date: Nov. 30, 2017

(65) Prior Publication Data
US 2019/0200917 A1  Jul. 4, 2019

(30) Foreign Application Priority Data
May 23, 2016 (GB) .................. 1609031

(51) Int. Cl.
*A61B 5/00* (2006.01)
*A61B 5/01* (2006.01)
(Continued)

(52) U.S. Cl.
CPC ............ *A61B 5/445* (2013.01); *A61B 5/0022* (2013.01); *A61B 5/0077* (2013.01); *A61B 5/015* (2013.01);
(Continued)

(58) Field of Classification Search
CPC ....... A61B 5/445; A61B 5/441; A61B 5/1032; A61B 5/442; A61B 5/443; A61B 5/7203;
(Continued)

(56) References Cited

U.S. PATENT DOCUMENTS 3,894,437 A * 7/1975 Hagy .................. A61B 5/1038
73/865.4
4,534,365 A * 8/1985 Bonetta ................ A61B 5/1074
600/592

(Continued)

FOREIGN PATENT DOCUMENTS

CN  105795602 A * 7/2016
CN  106132291 A * 11/2016 ............. A61B 5/015
(Continued)

OTHER PUBLICATIONS

Bharara, M., Cobb, J.E., & Claremont, D.J. (2006). Thermography and Thermometry in the Assessment of Diabetic Neuropathic Foot: A Case for Furthering the Role of Thermal Techniques. The International Journal of Lower Extremity Wounds, 5, 250-260. (Year: 2006).*
(Continued)

*Primary Examiner* — Jeffrey G Hoekstra
*Assistant Examiner* — Nicholas A Robinson
(74) *Attorney, Agent, or Firm* — Tarolli, Sundheim, Covell & Tummino LLP

(57) ABSTRACT

A skin inspection device for identifying abnormalities. The device comprises a transparent panel having an inspection area. An array of temperature sensors are provided on the transparent panel to record the temperature of an area of skin of a target. One or more image capture devices are provided for capturing an image of the area of skin of a target located in the inspection area. The captured image and recorded temperature being analysed to identify abnormalities in the
(Continued)

area of skin of the target. A processor is operably coupled to the one or more image capture devices and the array of temperature sensors for controlling operations thereof. The processor is operable to generate indicia indicative of the emergence of ulcers and/or other skin abnormalities.

41 Claims, 14 Drawing Sheets

(51) Int. Cl.
*A61B 5/103* (2006.01)
*G01G 19/50* (2006.01)
*G02F 1/13* (2006.01)

(52) U.S. Cl.
CPC .......... *A61B 5/1032* (2013.01); *A61B 5/1036* (2013.01); *A61B 5/441* (2013.01); *A61B 5/442* (2013.01); *A61B 5/443* (2013.01); *A61B 5/447* (2013.01); *A61B 5/7203* (2013.01); *A61B 5/7235* (2013.01); *A61B 5/746* (2013.01); *G01G 19/50* (2013.01); *G02F 1/132* (2013.01); *A61B 5/444* (2013.01); *A61B 2560/0223* (2013.01); *A61B 2562/0261* (2013.01); *A61B 2562/0271* (2013.01); *A61B 2562/0276* (2013.01); *A61B 2562/046* (2013.01); *A61B 2562/185* (2013.01); *A61B 2576/02* (2013.01)

(58) Field of Classification Search
CPC ..... A61B 5/7235; A61B 5/0022; A61B 5/746; A61B 5/0077; A61B 5/015; A61B 5/1036; A61B 5/447; A61B 2562/0276; A61B 2576/02; A61B 2562/185; A61B 2560/0223; A61B 2562/0261; A61B 2562/0271; A61B 2562/046; G02F 1/132; G01G 19/50
See application file for complete search history.

(56) References Cited

U.S. PATENT DOCUMENTS

| | | | | |
|---|---|---|---|---|
| 6,398,740 B1* | 6/2002 | Lavery | ............... | A61B 5/015 |
| | | | | 128/903 |
| 2002/0082486 A1* | 6/2002 | Lavery | ............... | A61B 5/01 |
| | | | | 600/300 |
| 2006/0186106 A1* | 8/2006 | Neville | ............... | G03G 15/18 |
| | | | | 100/92 |
| 2006/0283243 A1* | 12/2006 | Peterson | ............... | A61B 5/1036 |
| | | | | 73/172 |
| 2007/0211355 A1 | 9/2007 | Dalbo | | |
| 2009/0009595 A1* | 1/2009 | Ishiwata | ............... | A61B 5/0075 |
| | | | | 348/E7.085 |
| 2013/0194261 A1* | 8/2013 | Cummins | ............... | G06T 11/001 |
| | | | | 345/420 |
| 2013/0211283 A1* | 8/2013 | Bunch | ............... | A61B 5/6853 |
| | | | | 600/549 |
| 2013/0261496 A1 | 10/2013 | Engler | | |
| 2014/0121479 A1* | 5/2014 | O'Connor | ............... | A61B 5/447 |
| | | | | 600/407 |
| 2015/0150457 A1* | 6/2015 | Wu | ............... | A61B 5/445 |
| | | | | 600/425 |
| 2016/0105644 A1* | 4/2016 | Smith | ............... | G08B 29/185 |
| | | | | 348/159 |
| 2016/0135981 A1* | 5/2016 | Rizzo | ............... | A61F 5/14 |
| | | | | 12/142 N |
| 2016/0166150 A1* | 6/2016 | Vilenskii | ............... | H04N 5/2251 |
| | | | | 348/77 |
| 2016/0192844 A1* | 7/2016 | Linders | ............... | A61B 5/7282 |
| | | | | 600/549 |
| 2016/0299061 A1* | 10/2016 | Goldring | ............... | G01J 3/0256 |
| 2017/0127999 A1* | 5/2017 | Linders | ............... | A61B 5/7405 |
| 2019/0209093 A1* | 7/2019 | Watts | ............... | A61B 5/1078 |
| 2019/0281204 A1* | 9/2019 | Darty | ............... | A61B 5/443 |
| 2019/0290496 A1* | 9/2019 | Brownhill | ............... | A61F 13/0216 |

FOREIGN PATENT DOCUMENTS

| | | | | |
|---|---|---|---|---|
| DE | 102012101054 A1 * | 8/2013 | ............... | A61B 5/015 |
| DE | 102015215221 B3 * | 12/2016 | ............... | A61B 5/0035 |
| FR | 2516779 A * | 5/1983 | ............... | A61B 5/015 |
| JP | H1124170 A * | 4/1997 | | |
| JP | 2006010320 A * | 1/2006 | | |
| JP | 2008224670 A * | 9/2008 | ............... | A61B 5/6804 |
| KR | 20070048759 A * | 5/2007 | ............... | A61B 5/445 |
| WO | WO-2008110949 A1 * | 9/2008 | ............... | A61B 5/6833 |

OTHER PUBLICATIONS

Bharara, M. (2007). Liquid crystal thermography in neuropathic assessment of the diabetic foot. (Year: 2007).*

International Search Report and Written Opinion for corresponding International Application No. PCT/EP2017/058294, dated Jul. 10, 2017.

* cited by examiner

SKIN INSPECTION DEVICE FOR IDENTIFYING ABNORMALITIES

RELATED APPLICATIONS

The present invention is a U.S. National Stage under 35 USC 371 patent application, claiming priority to Serial No. PCT/EP2017/058294, filed on 6 Apr. 2017; which claims priority of GB 1609031.8, filed on 23 May 2016, the entirety of both of which are incorporated herein by reference.

FIELD OF THE INVENTION

The present invention relates to a skin inspection device for identifying abnormalities. In particular, but not exclusively, the skin inspection device relates to heat sensing a sole of a human foot in order to predict the formation of ulcers.

BACKGROUND

Diabetics commonly suffer from a condition known as diabetic foot ulcers (DFU) over their lifetime. It is recommended that diabetics inspect their feet daily so as detect any abnormal damage to the skin that may be an indicator of the onset of DFU. However, limiting factors such as reduced vision, reduced mobility, lack of sensation due to peripheral neuropathy, and a lack of education results in diabetics failing to adhere to daily foot inspections as recommended. Early identification of DFUs may result in improved outcomes and reduced medical treatment costs. If DFUs are detected before they form the benefit would be even greater. Currently the best practice is to visually inspect the feet and report to a podiatrist periodically.

Temperature monitoring is a known method of predicting DFU formation. A temperature difference of 2.2° C. between similar points on opposite feet has been shown to indicate inflammation which may be a precursor to ulceration. Temperature point probes are known in the art which allow patients to take temperatures on the bottom of both feet so that temperature comparisons may be made from spot to spot. Such point probes may be used to measure skin temperature at individual target spots. If a spot on one foot demonstrates a change in temperature, compared to the same spot on the other foot, and sustains that change in temperature or higher (rises to four degrees Fahrenheit (2.2° C.) or more for two days or more) it indicates that a problem may be occurring and the patient is alerted to consult their doctor. The difficulty with this approach is that the same spot of the patients foot requires to be measured over a number of days. It is difficult for a patient to identify the same spot in order to accurately take measurements. Furthermore, the onus is on the patient to maintain a log of the temperature readings in order to do the comparisons which may result in human error. Daily visual inspection of the feet is recommended for all diabetics. As mentioned, this can be difficult due to poor vision and mobility. Current temperature monitoring devices do not facilitate the recommended daily visual inspection.

There is a need for a skin inspection device which addresses at least some of the drawbacks of the prior art.

SUMMARY

The present disclosure relates to a skin inspection device for identifying abnormalities; the device comprising:
a transparent panel having an inspection area;
an array of temperature sensors provided on the transparent panel to record the temperature of an area of skin of a target;
one or more image capture devices for capturing an image of the area of skin of a target located in the inspection area; the captured image and recorded temperature being analysed to identify abnormalities in the area of skin of the target; and
a processor operably coupled to the one or more image capture devices and the array of temperature sensors for controlling operations thereof;
wherein the processor is operable to generate indicia indicative of the emergence of ulcers and/or other skin abnormalities.

In one aspect, the array of temperature sensors have associated addressable coordinates.

In another aspect, the processor is operable to associate one or more regions of the captured image to one or more addressable coordinates.

In a further aspect, the temperature sensors are spaced apart to facilitate optical transmission therebetween.

In one aspect, optical pathways are provided between adjacent temperature sensors. Advantageously, optical pathways are defined by a region between two or more adjacent temperature sensors.

In an exemplary aspect, a strain gauge is provided operable for detecting a weight bearing load on the transparent panel. Advantageously, the processor is configured to activate the image capture device in response to the strain gauge detecting a weight bearing load.

In one aspect, a housing is provided on which the transparent panel is mounted. Advantageously, the housing accommodates the processor and the one or more image capture devices therein.

In a further aspect, the transparent panel provides a foot plate of sufficient strength to support the weight of an adult human.

In one aspect, the transparent panel is rigid.

In an alternative aspect, the transparent panel is of a resilient material operable to conform to the shape of a sole of a foot when stepped on by an individual.

In one aspect, the temperature sensors are provided on an upper surface of the transparent panel.

In another aspect, the temperature sensors are mounted on the transparent panel.

In an exemplary arrangement, a calibration means is provided.

In one aspect, the processor is configured to process the image captured by the image capture device for determining the temperature of the area of skin of the target at multiple discrete locations.

In another aspect, the processor is configured to generate a temperature dataset based on the temperature of the area of skin of the target at the multiple discrete locations.

In a further aspect, the temperature dataset includes the temperatures recorded by the array of temperature sensors.

In an exemplary aspect, the processor is configured to associate temperature values in the temperature dataset with locations on the captured image of the target.

In one aspect, the processor is configured to perform analysis on the temperature dataset and the captured image.

In another aspect, the analysis compares the temperature at similar points of the captured image.

In a further aspect, the processor is operable to generate indicia indicative of the emergence of ulcers and/or other skin abnormalities at particular locations on the captured image.

In one aspect, the indicia comprises the temperature dataset.

In another aspect, the processor is configured to detect for areas on the captured images including at least one of excess callous, blisters, moisture, and discolouration.

In a further aspect, an alert mechanism is provided for generating an alert. Advantageously, the alert mechanism is operable to communicate the alert to a remote entity via a telecommunications network.

In one aspect, the image capture device is triggered to capture an image in response to an input. Advantageously, the image capture device is triggered to capture an image in response to a foot being placed on the inspection area.

In a further aspect, the temperature sensors are spaced at approximately 1 per 1 cm². Advantageously, the density of temperature sensors is in the range of between 0.5 and 6 per cm². In one example, each temperature sensor has a diameter in the range of 0.1 mm to 4 mm.

In another aspect, the transparent panel comprises glass; a composite material; polycarbonate or other plastics material.

In a further aspect, one or more calibration components are provided.

In an exemplary aspect, a light source is provided.

In one aspect, a light filter is provided to alter light intensity entering a field of view of the image capture device.

In another aspect, the light source comprises one or more LEDs Light-Emitting Diodes (LEDs) of a known intensity and colour.

In a further aspect, one or more diffusion films are provided for reducing glare on the transparent panel.

In one aspect, foot shaped panels are provided.

In a further aspect, a plurality of image capture devices are used to capture the image of the target.

In one aspect, two or more image capture devices are provided with an area of overlap in the field of view.

In another aspect, a calibration target is located in the overlap field of view.

In one aspect, a light sensor is provided within a field of view of the image capture device.

In another aspect, the output from the light sensor is used by the processor to modify the operational settings of the image capture device.

In a further aspect, the output from the light sensor is used as an input by a post processing algorithm to eliminate the effects of ambient light.

In another aspect, a heat sensor is provided for sensing the temperature of the transparent panel.

In one aspect, one or more baffles are configured to block at least a portion of glare-causing rays of light.

In one aspect, the one or more baffles are selectively adjustable. Advantageously, the dimensions, orientation, configuration or location of the one or more baffles are selectively adjustable.

The present disclosure also relates to a weighing scales comprising
  a means for calculating the weight of an individual; and
  a skin inspection for identifying abnormalities; the device comprising:
    a transparent panel having an inspection area;
    an array of temperature sensors provided on the transparent panel to record the temperature of an area of skin of a target;
    one or more image capture devices for capturing an image of the area of skin of a target located in the inspection area; the captured image and recorded temperature being analysed to identify abnormalities in the area of skin of the target; and
    a processor operably coupled to the one or more image capture devices and the array of temperature sensors for controlling operations thereof;
    wherein the processor is operable to generate indicia indicative of the emergence of ulcers and/or other skin abnormalities.

These and other formations will be better understood with reference to the followings Figures which are provided to assist in an understanding of the present teaching.

BRIEF DESCRIPTION OF THE DRAWINGS

The present teaching will now be described with reference to the accompanying drawings in which.

DETAILED DESCRIPTION OF THE DRAWINGS

Figure 1:
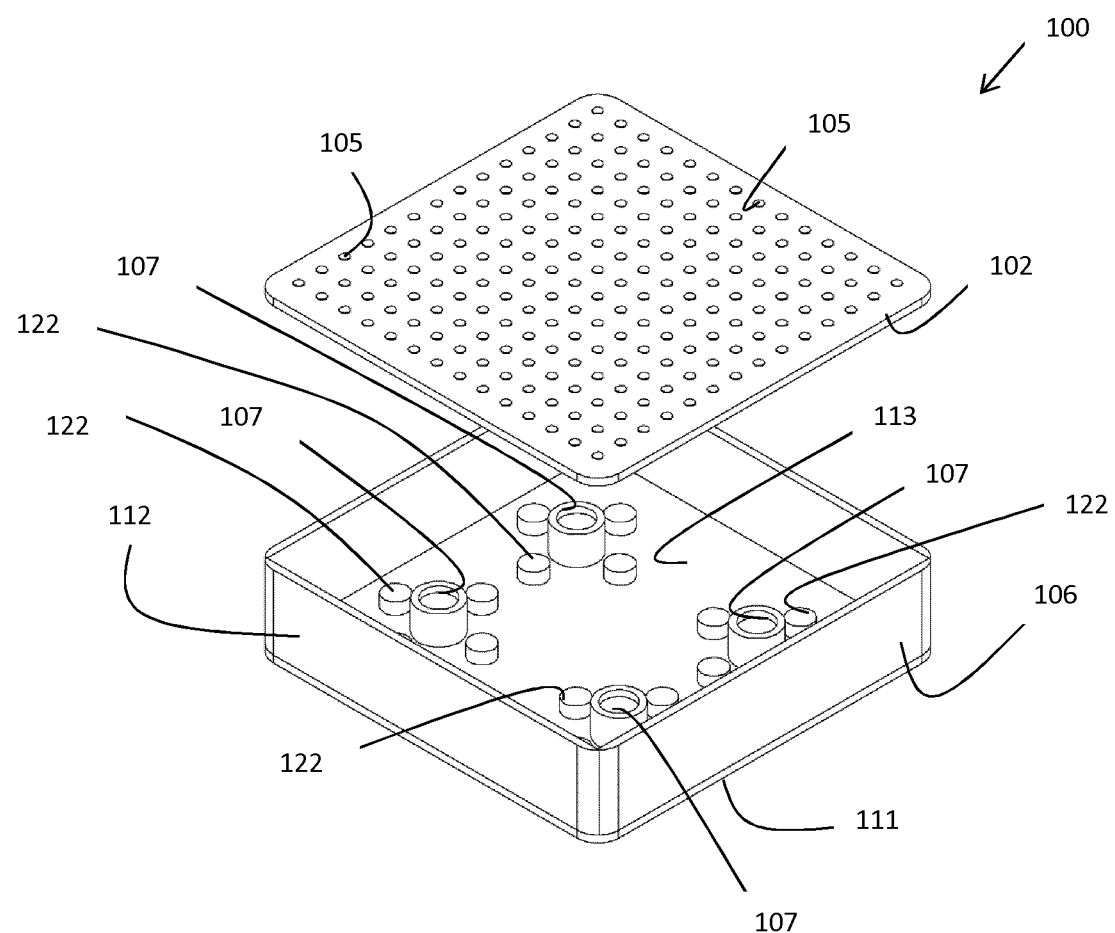
FIG. 1 illustrates a skin inspection device in accordance with the present disclosure.

The present invention will now be described with reference to some exemplary skin inspection devices. It will be understood that the exemplary skin inspection devices are provided to assist in an understanding of the teaching and is not to be construed as limiting in any fashion. Furthermore, elements or components that are described with reference to any one Figure may be interchanged with those of other Figures or other equivalent elements without departing from the spirit of the present teaching. It will be appreciated that for simplicity and clarity of illustration, where considered appropriate, reference numerals may be repeated among the figures to indicate corresponding or analogous elements.

Figure 2:
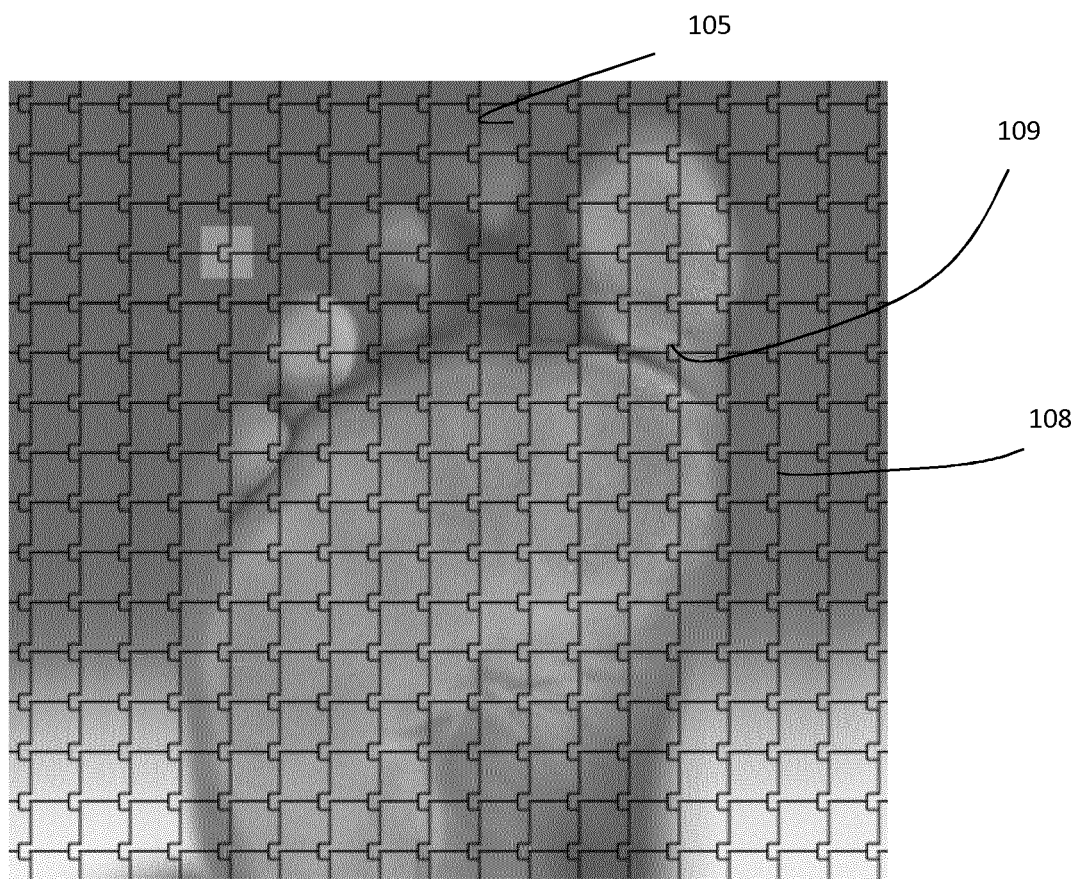
FIG. 2 is a graphical representation of a detail of the device of FIG. 1.
Figure 3:
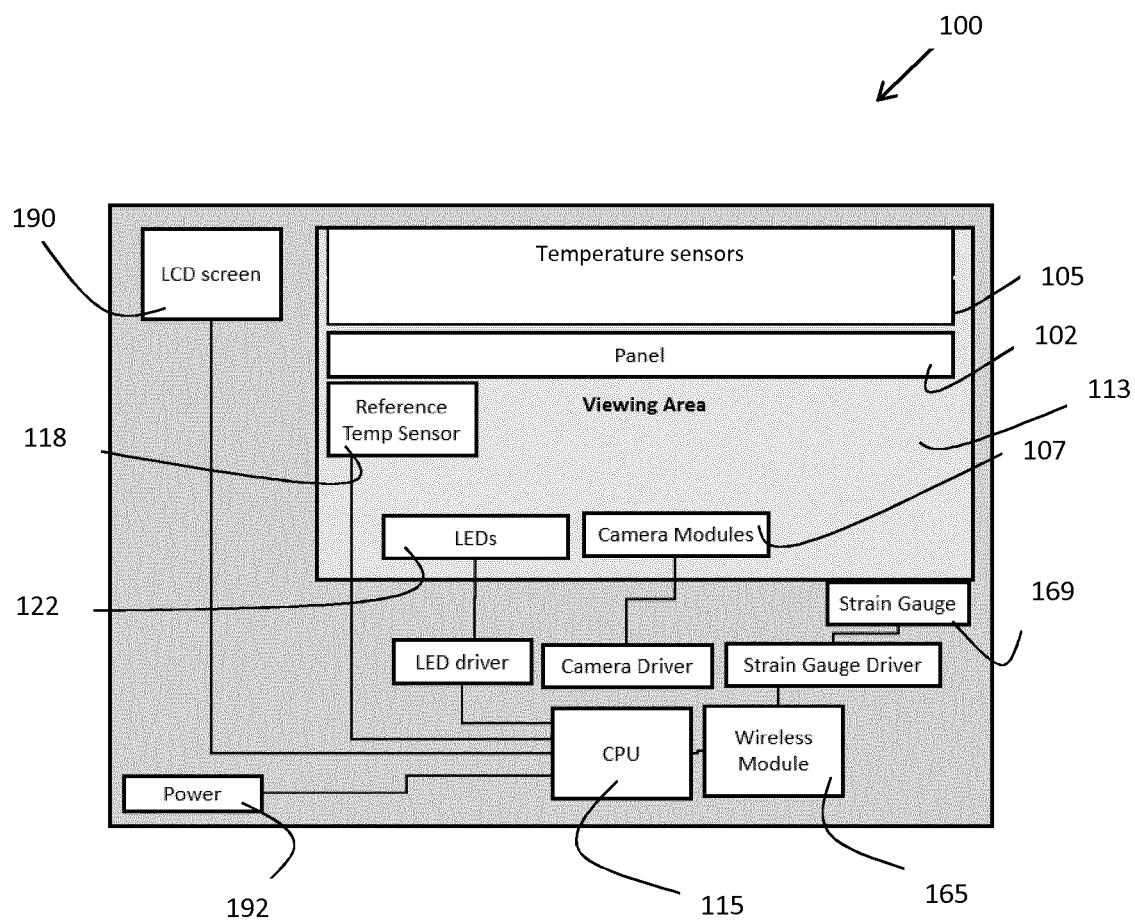
FIG. 3 is a block level diagram of details of the device of FIG. 1.

Referring to the drawings there is illustrated a skin inspection device 100 for identifying the formation of abnormalities in accordance with the present teaching. The device 100 comprises a transparent panel 102 which defines an inspection area for co-operating with a region of a body under inspection. For example, the region under inspection may be a foot, a hand, an arm, a leg, etc. In the exemplary arrangement, the region under inspection is a sole of a foot 109 as illustrated in FIG. 2. The transparent panel 102 provides a foot plate which accommodates the foot 109 during inspection. However, it is not intended to limit the present teaching to feet as other regions may also be inspected by the device 100. An array of temperature sensors 105 are provided on the transparent panel 102 which are operable to record the temperature of an area of skin of the foot 109 during inspection.

The transparent panel 102 is supported on a housing 106 which accommodates the components of the device 100 therein. The housing 106 comprises a base 111 with side walls 112 extending upwardly therefrom which together define a hollow interior region 113. One or more image capture devices 107 are provided in the hollow interior region 113 for capturing an image of the temperature sensors and an area of skin of the foot 109 in contact with the transparent panel 102. One or more light sources in the form of LEDs 122 may also be located within the hollow interior region 113. Other types of light sources other that LEDS may be used such as cold cathode lamps, electroluminescent coated materials, for example, tapes, panels, wires, xenon or halogen bulbs. A central processing unit 115 is also provided within the hollow interior region 113 and is configured to control the operations of the device 100 as described in detail below.

In the exemplary embodiment, the temperature sensors 105 are provided on the transparent panel 102 as printed flexible electronic components. In the exemplary embodiment, the temperature sensors 105 are either printed directly onto the transparent panel 102 or printed onto a transparent overlay film, such as 0.01 mm PET, which is subsequently attached to the transparent panel 102. Any type of temperature sensor may be used such as, but not limited to contact or non-contact sensors, RTD, thermocouples, thermopiles, thermistors, semiconductor, microbolometers, thermochromic liquid crystal. It will be appreciated by those skilled in the art that the temperature sensors may be provided on the panel using techniques other than printing which is described by way of example only. The array of temperature sensors 105 are provided on the upper side of the transparent panel 102 such that they easily come in to contact with the region of the body under inspection, namely the sole of the foot 109. The sensors 105 and their connection wires/traces are arranged in such a way as to provide maximum visibility through the transparent panel to the image capture devices 107. The sensors 105 are typically arranged in a grid with a 0.5-2 cm pitch. This has been found to provide adequate resolution to record the temperature of an area of skin of the foot 109. In an alternative arrangement, the temperature sensors 105 are provided on the underside of the transparent panel 102. In such an arrangement, the panel 102 may be made from Infra-red (IR) transparent material or contain holes to allow IR radiation to pass through. In another arrangement, the section of the transparent panel 102 may be made from a highly conductive material to facilitate heat transfer from one side of the transparent panel 102 to the other, such that temperature sensors 105 on the underside of the transparent panel 102 may determine the temperature on the upper side of the transparent panel 102.

The transparent panel 102 is configured to have sufficient strength to support the weight of an adult human. The transparent panel 102 may be a rigid material such as glass; a composite; polycarbonate or other plastics material, or the like. As the foot 109 is a three dimensional shape with various contours, for example the arch, the entire sole of the foot 109 would not be in contact with the temperature sensors 105. In order to improve the contact between the temperature sensors 105 and the foot 109 the panel 102 may be manufactured from a flexible or resilient material that would conform to the shape of the sole of the foot 109. A material such as clear silicone may be used as it is both optically transparent and resilient. For example, the panel may conform to match the shape of the arch of the users foot 109. This would allow more contact with the temperature sensors. In an exemplary arrangement the panel may include one or more formations for engaging with the foot in order to enhance the area of the foot that is in contact with the temperature sensors 105. For example, the one or more formations may include one or more indentations or one or more projections or a combination of indentations and projections. It is not intended to limit the present teaching to silicone as other materials with similar properties may be used as would be understood by those skilled in the art. The temperature sensors 105 could then be printed onto this layer in the same fashion as outlined above.

When a rigid transparent panel 102 is used the temperature sensors 105 will be located in the same XY locations relative to the image capture device 107. However, with a resilient panel 102 the temperature sensors 105 may shift slightly in the X and Y directions and more dramatically in the Z direction. In this arrangement, the CPU 115 may be configured to apply an algorithm that would scan the captured image and automatically identify the location of temperature sensors 105 and then use the updated locations in subsequent processing steps.

Various calibration features may be incorporated into the device 100 to improve accuracy. In order to maximise accuracy, the device 100 may include features to mitigate the effects of environmental light, light temperature and viewing angle on the captured colour. Various calibration techniques may be used to mitigate against these effects. In addition to this, various methods can be used to control the lighting environment within the hollow interior region 113 which may be considered as a "viewing area" for the image capture device 107. Calibration targets may be used in a multiple camera configuration device. This would enable matching the brightness and colour reproduction. Another option is to use a master slave camera configuration, to match setting across multiple cameras. Another potential configuration is to use two or more cameras with an area of overlap in the field of view, and the calibration target placed in this overlap section.

An embodiment of the skin inspection device according to the invention will now be described in use. To inspect the sole of the foot 109, a user steps onto the transparent panel 102 of the device 100. The sole of the user's foot 109 comes into contact with the temperature sensors 105 allowing the temperature of an area of skin on the sole of the foot which contacts a temperature sensor to be recorded. The temperature sensors 105 are arranged on the transparent panel 102 in a grid formation such that adequate measurements of temperature can be taken at multiple discrete locations on the sole of the foot 109. A digital photographic image of the temperature sensors 105 and the sole of the foot 109 under inspection is taken by the image capture device 107. The spacing of the temperature sensors 105 is such that a high resolution digital image of the sole of the foot 109 can be captured. The array of temperature sensors 105 have associated addressable coordinates. The CPU 115 is operable to associate one or more regions of the captured image to one or more addressable coordinates. The temperature sensors 105 are spaced apart to facilitate optical transmission therebetween. The optical pathways are provided between adjacent temperature sensors 105. The optical pathways may be defined by a region between two or more adjacent temperature sensors 105. In an exemplary arrangement, it is desirable to maximise the size of the optical pathways between the temperature sensors 105, in order to maximise the area of skin visible to the image capture device 107. The area of skin visible to the image capture device 107 is inversely proportional to the area of the temperature sensors 105 which occlude light transmission through the transparent panel 102. In this way it is advantageous to maximise the area of the optical pathway while minimising the area of occluded by the temperature sensors 105. It will be appreciated by those skilled in the art, that such an arrangement will facilitate an increased detection of abnormalities as more area of the skin can be viewed by the image capture device 107.

In one exemplary arrangement the temperature sensors may be spaced at 1 per 1 cm$^2$. In another arrangement the temperature sensors may spaced in the range of between 0.5 and 6 per cm$^2$. For example, each temperature sensor 105 has a diameter in the range of 0.1 mm to 4 mm. It will be appreciated that the sensors may be interconnected by electrical conductors 108 and the area occupied by the electrical conductors 108 should be minimised to maximise the size of the optical pathway between the temperature sensors 105. In one exemplary arrangement, the temperature sensors 105 are arranged in a matrix formation comprising rows and columns. The electrical conductors 108 extend along the rows and columns and define addressable temperature sensors 105. It will be appreciated by those skilled in the art that it is not intended to limit the present teaching to the exemplary values provided, which are provided by way of example only.

The CPU 115 is configured to generate a temperature dataset comprising the recorded temperature values of the temperature sensors 105. The CPU 115 is further configured to associate temperature values in the temperature dataset with locations on the captured image of the target. Each temperature value is therefore associated with a known co-ordinate or range of co-ordinates in the digital image. The temperature sensors 105 record temperature at various points on the foot 109. If a point on one foot demonstrates a change in temperature, compared to the same point on the other foot, and sustains that change in temperature or higher (rises to four degrees Fahrenheit (2.2° C.) or more for two days or more) the CPU 115 may be configured to indicate that a DFU problem may be occurring and the patient is alerted to consult their doctor.

In a configuration where the temperature sensors 105 are placed onto a transparent panel 102 made of glass, plastic or the like, it would be advantageous to know the panel temperature in order to offset for this temperature on the sensors reading. A sensor 118 may be placed on the transparent panel 102 or a proximity IR sensor pointed at the panel 102 could be used to obtain the panel temperature.

Figure 4:
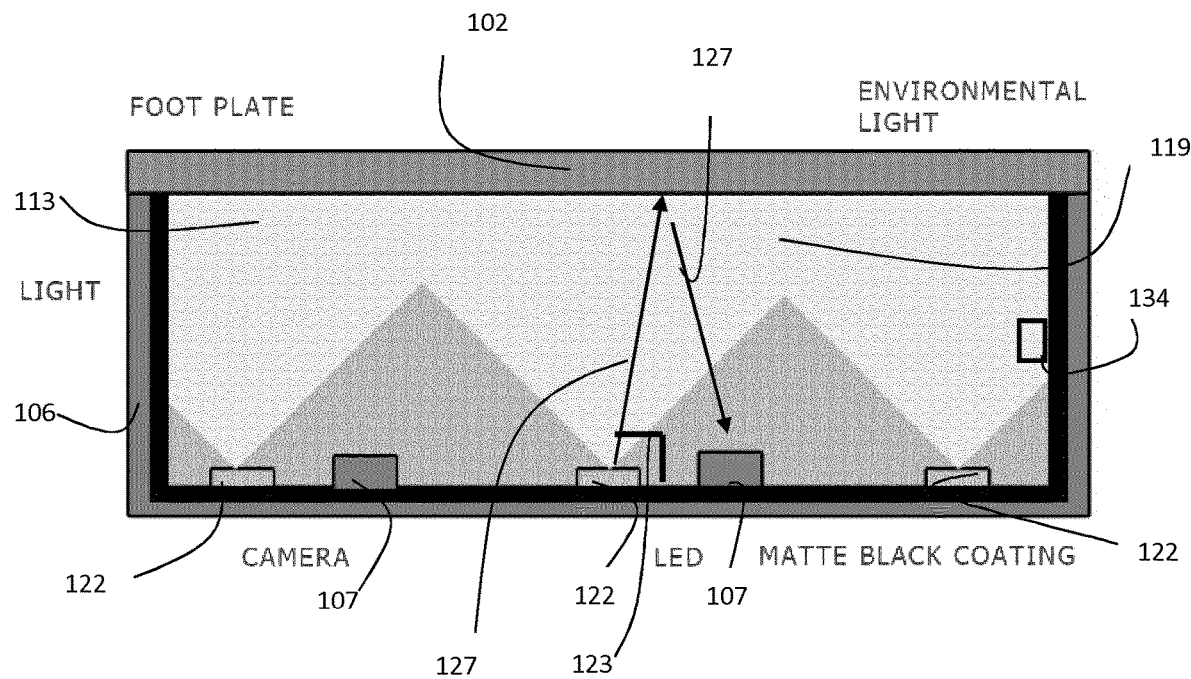
FIG. 4 illustrates another skin inspection device which is also in accordance with the present teaching.
Figure 5:
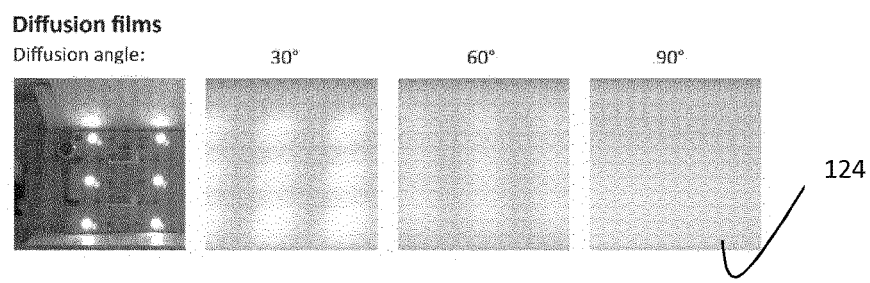
FIG. 5 illustrates a detail of the skin inspection device of FIG. 4.

A series of LEDs 122 as illustrated in FIG. 4 may be placed within the hollow interior region 113 and may act to override the environmental lighting conditions. The LEDs 122 may be of a known intensity and colour to produce repeatable conditions for viewing the temperature sensors 105. In addition to standard LED lights, one or more diffusion films 124 may be provided to reduce the glare on the transparent panel 102 coming from the LEDs 122 and to provide a uniform level of lighting across the entire surface of the panel 102. Another alternative method of reducing glare is to tailor the position of the target, the image capture device 107, and the illumination source. To minimise glare, the preferable arrangements are those which minimise the amount of light reflected by the illumination source onto the image capture device 107.

Another alternative method of reducing glare is to provide one or more structures such as baffle(s) 123 which block the rays of light from the illumination source 122, which will reflect directly onto the image capture device 107. The baffle 123 may be advantageously constructed in a manner which minimises the size of the shadow cast, which ensuring that the shadow is sufficiently large to block glare-causing rays of light 127. It is intended that the baffle 123 is configured to block substantially all the glare-causing rays of light 127. However in some arrangements the baffles 123 may be configured to selectively block a portion of the glare-causing rays of light 127. The baffle 123 ensures that the amount of illumination of the area where the target is located is controlled to a desired level. In this way the glare is controlled to a desired level. The location of the baffle 123 may be fixed or adjustable. A mechanism may be provided for facilitating selectively moving the baffles to desired locations. The dimensions of the baffle 123 may be fixed or adjustable. It will be appreciated that the baffle 123 may be selectively adjustable. It is envisaged that the dimensions, configuration, orientation, or location of the baffle 123 may be selectively adjustable as desired.

Figure 6:
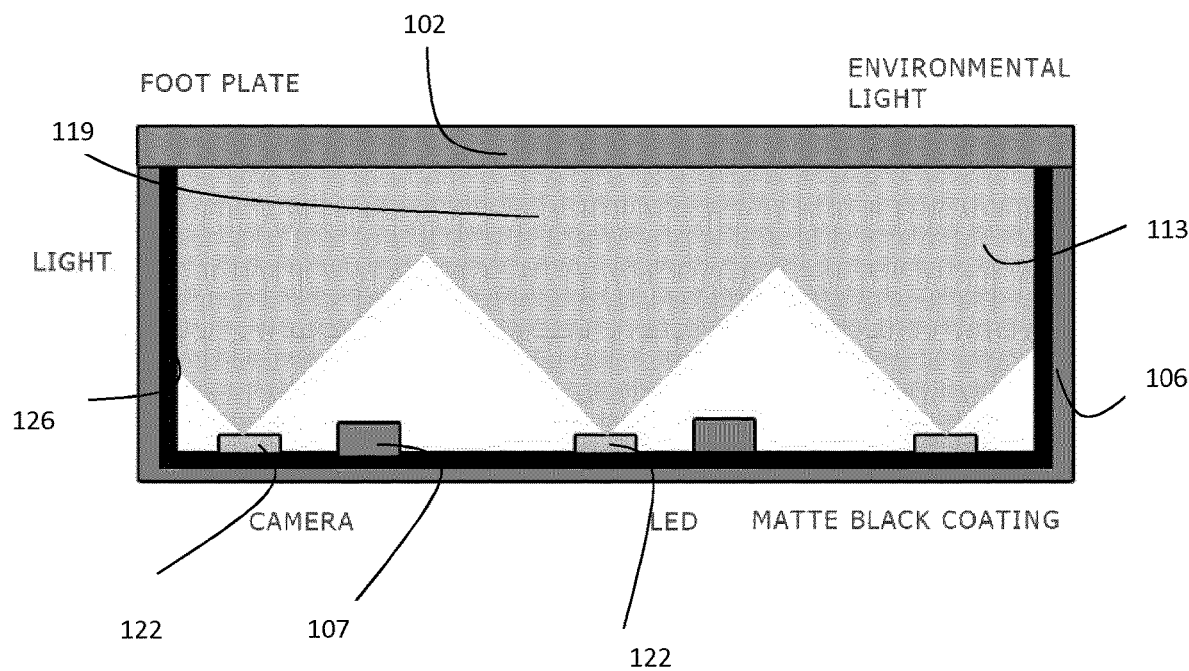
FIG. 6 illustrates another skin inspection device which is also in accordance with the present teaching.

Referring now to FIG. 6, which illustrates an exemplary skin inspection device which is also in accordance with the present teaching. In this exemplary arrangement, all internal surfaces of the housing 106 is coated with a low reflection material 126 so that the amount of light reflected off the internal surfaces of the housing 106 is minimised. This will reduce the amount of external light that is reflected onto the target from below.

Figure 7A:
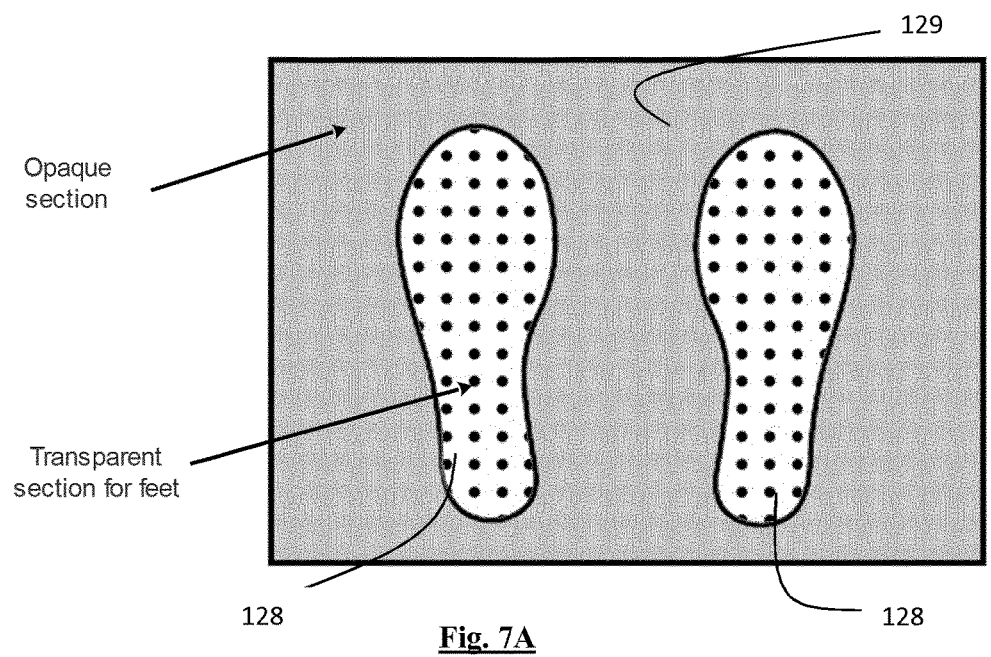
FIG. 7A illustrates exemplary details of a skin inspection device in accordance with the present teaching.
Figure 7B:
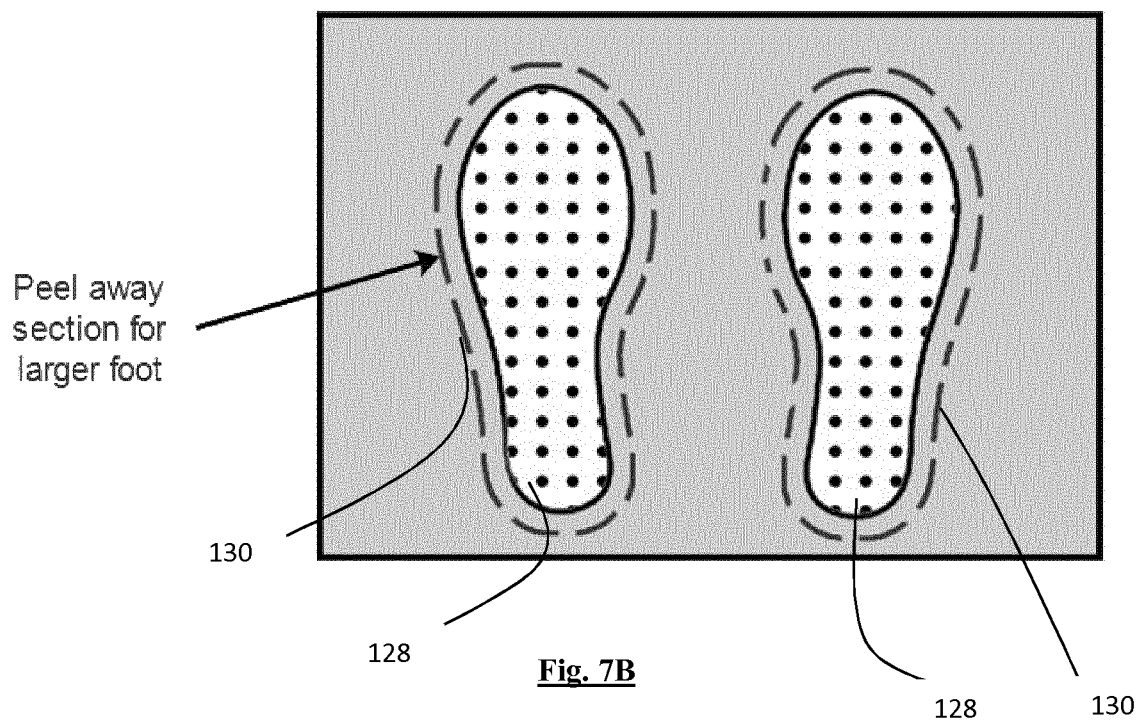
FIG. 7B illustrates exemplary details of a skin inspection device in accordance with the present teaching.

Referring now to FIGS. 7A-7B which illustrates an exemplary skin inspection device which is also in accordance with the present teaching. In order to limit the amount of environmental light entering the viewing area 119 the user could be instructed to step into foot shaped panels 128 as opposed to a large open panel. The foot shape panels 128 may be made of a transparent material while the remaining area 129 would be opaque. The opaque area would not allow environmental light to enter the viewing area 119. Similarly, when the foot 109 is placed on the foot shaped panel 128 it would obstruct light from entering the viewing area. It may be beneficial for the device 100 to be stored and transported with a protective opaque cover 130. The cover 130 may have 'peel-away' sections which are of different foot sizes. The user would peel away the necessary sections to match the size of their feet. This would limit the amount of ambient light that can enter the device.

A light sensor 134 may be placed within the viewing area 119 of the device 100. This light sensor 134 could detect the intensity of ambient light acting on it. One example of such a sensor is the Grove Light Sensor from Seed Studio. This sensor can detect light intensity as well as an approximate lux value. The output from this sensor can be used by the CPU 115 to modify the image capture device 107 settings to react to the environmental light. It can also act as an input for a post processing algorithm to eliminate the effects of ambient light on sensor readings. The light sensor 134 could be activated by the device 100 as a photographic image is being taken. Alternatively, the light sensor 134 could be activated prior to the user stepping on the panel 102. In this scenario the user would activate the device 100 and wait for it to perform a light intensity test before stepping onto the panel 102.

Figure 8:
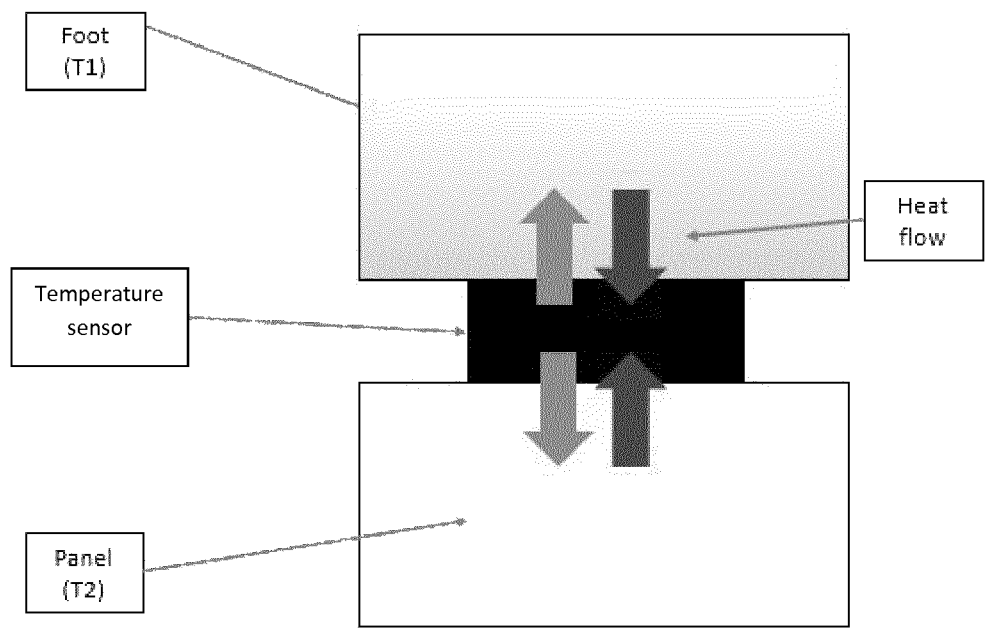
FIG. 8 illustrates exemplary details of a skin inspection device in accordance with the present teaching.

The temperature of the panel 102 could potentially impact the temperature of the temperature sensors 105 to give false temperature readings. The temperature sensors will be thermally acted on by the foot 109 as well as the panel 102, with the panel 102 acting to either increase or decrease the sensor temperature as illustrated in FIG. 8. In order to isolate the panel temperature 102 from the sensor temperature it is beneficial to know the temperature of the panel 102 itself. The panel temperature or reference temperature could be recorded in a number of ways. This temperature value would be input into an algorithm which would be applied to the recorded temperature values from the temperature sensors. This algorithm would eliminate the effect of the panel temperature on the recorded sensor temperature.

Figure 9:
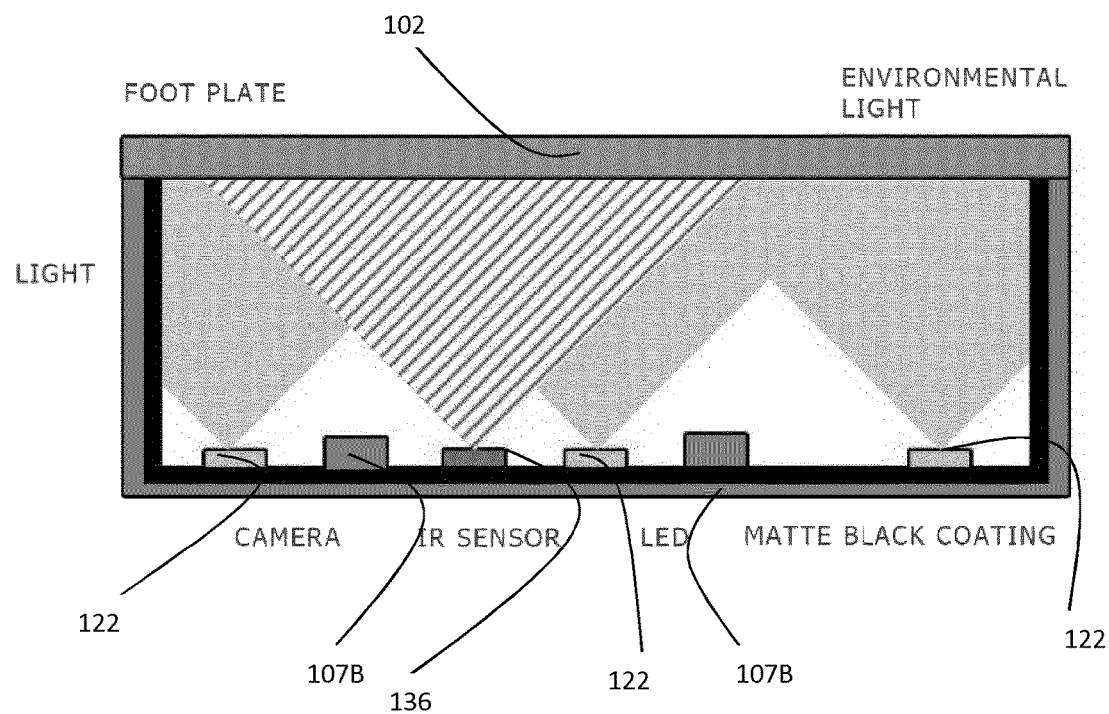
FIG. 9 illustrates exemplary details of a skin inspection device in accordance with the present teaching.
Figure 10:
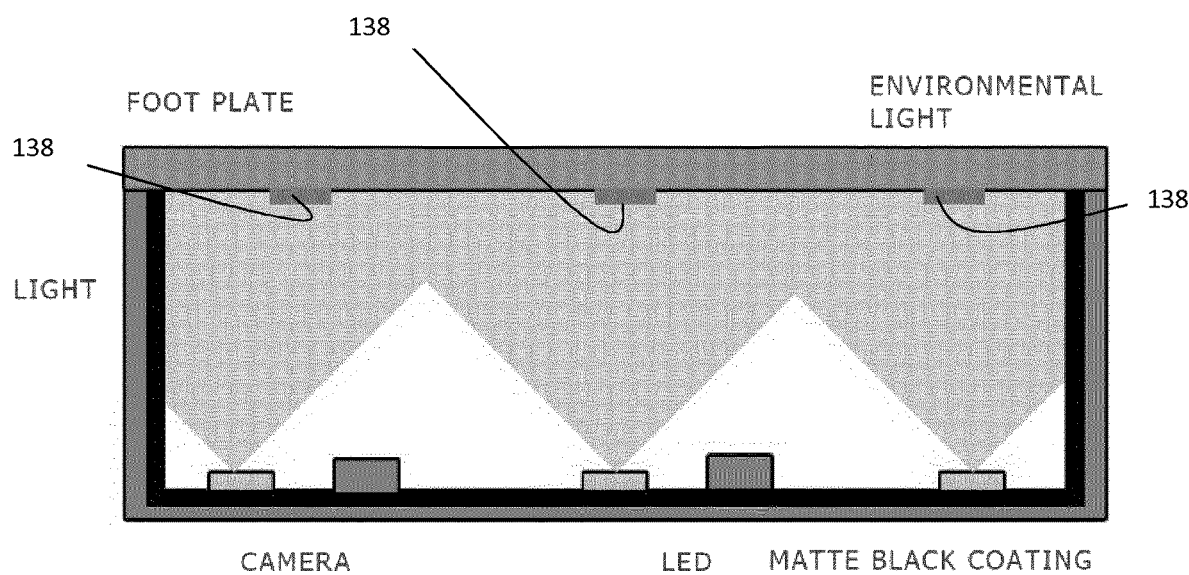
FIG. 10 illustrates another skin inspection device which is also in accordance with the present teaching.

One method uses an infrared temperature sensor 136 pointed at the panel 102 as illustrated in FIG. 9. This would allow a relatively large area of the panel 102 to be analysed for its temperature. There may be a risk that the temperature of the panel 102 is not continuous across the entire surface. In order to determine this a number of temperature measurements can be taken by a number of temperature sensors. An alternative method of determining temperature is by using a thermistor or thermocouple 138 that is mounted on the panel as illustrated in FIG. 10. A number of these sensors 138 could be used to determine if the temperature of the entire panel is continuous.

A further alternative method of recording the panel temperature could involve the use of the temperature sensors themselves. The CPU 115 may apply an algorithm to identify sensors which are sufficiently far from the foot. If the recorded temperature values differ significantly across the entire surface the device may alert the user that the temperature of the panel is not continuous and instruct them to move to an area where a more stable temperature can be achieved. For example, the temperature may not be continuous because the device has been left beside a radiator or in direct sunlight.

In addition to the methods described above, there could be a method whereby instead of the device being activated by the users weight it is activated by a button. Once pressed, the device 100 could take a temperature reading to determine the panel temperature. The advantage of this is that the warmth of the patients' feet will not impact this temperature reading. In addition to this temperature reading a light intensity reading may also be taken.

Figure 11:
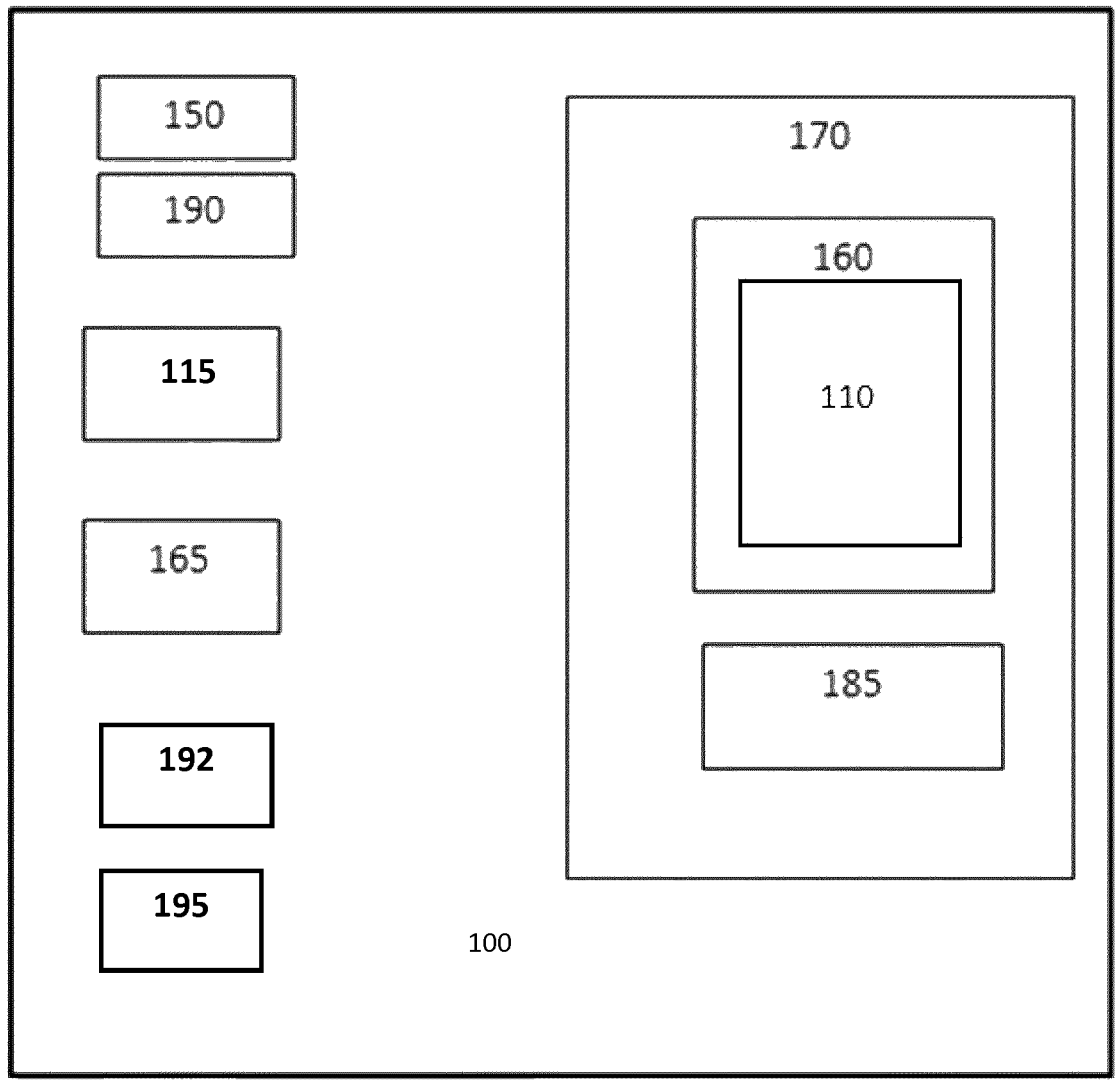
FIG. 11 illustrates exemplary components of a skin inspection device in accordance with the present teaching.
Figure 12:
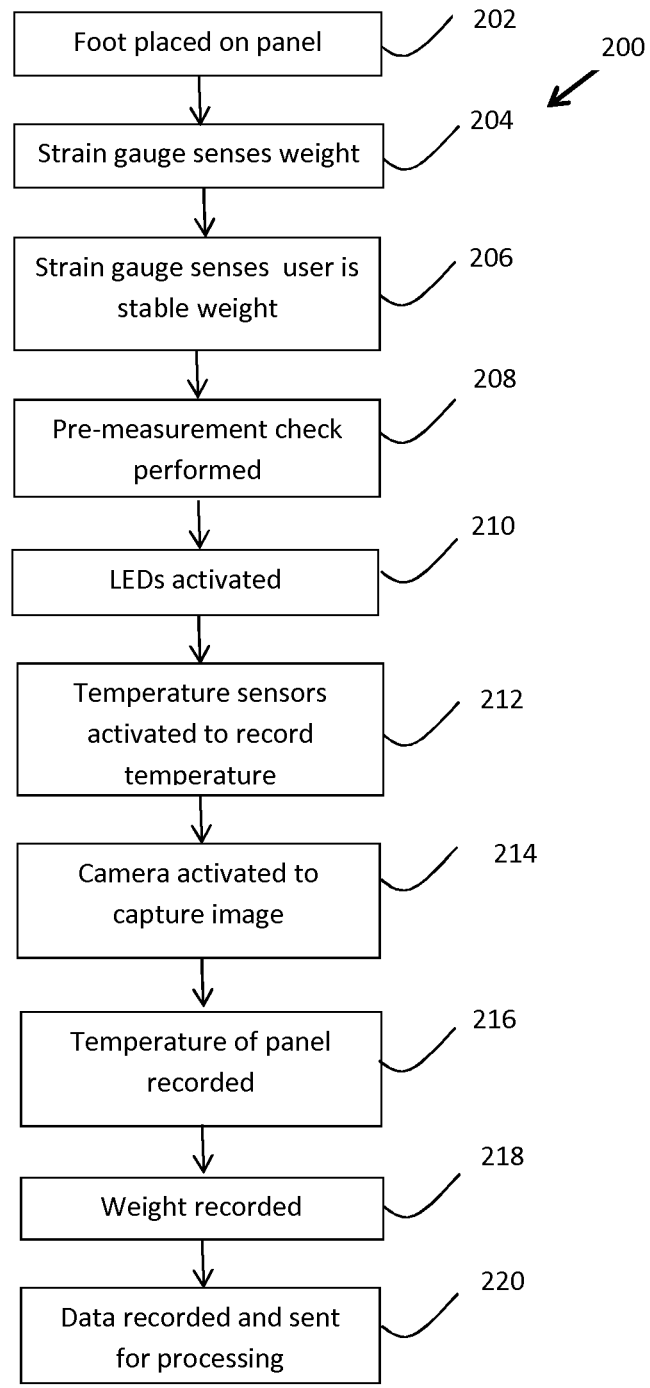
FIG. 12 is a flow chart detailing exemplary steps carried by a skin inspection device in accordance with the present teaching.

It will be appreciated that the device 100 includes one or more software modules which are programmed to implement predefined functions. The device 100 as illustrated in FIG. 11 may include various hardware and software components that function to perform the methods according to the present disclosure. The device 100 comprises a user interface 150, CPU 115 in communication with a memory 160, and a communication interface 165. The CPU 115 functions to execute software instructions that can be loaded and stored in the memory 160. The CPU 115 may include a number of processors, a multi-processor core, or some other type of processor, depending on the particular implementation. The memory 160 may be accessible by the CPU 115, thereby enabling the CPU 115 to receive and execute instructions stored on the memory 160. The memory 160 may be, for example, a random access memory (RAM) or any other suitable volatile or non-volatile computer readable storage medium. In addition, the memory 160 may be fixed or removable and may contain one or more components or devices such as a hard drive, a flash memory, a rewritable optical disk, a rewritable magnetic tape, or some combination of the above.

One or more software modules 170 may be encoded in the memory 160. The software modules 170 may comprise one or more software programs or applications having computer program code or a set of instructions configured to be executed by the processor 115. Such computer program code or instructions for carrying out operations for aspects of the systems and methods disclosed herein may be written in any combination of one or more programming languages. During execution of the software modules 170, the CPU 115 configures the device 110 to perform various operations relating to identifying the formation of skin abnormalities according to embodiments of the present disclosure. The CPU 115 may be configured to process the image captured by the image capture device 107 for determining the temperature of the target at multiple discrete locations. Additionally, the CPU 115 may be configured to generate a temperature map based on the temperature values. In one exemplary arrangement, the CPU 115 is operable to overlay the temperature map onto the captured image of the target. In another arrangement, the CPU 115 is configured to perform image analysis on the temperature map and the captured image. The CPU may be programmed to compare the temperature at similar points of the captured image. The CPU 115 may be operable to generate indicia indicative of the emergence of ulcers and/or other skin abnormalities based on image analysis of the captured image. The indicia may be in the form of an output image, for example. The CPU 115 may be operable to generate indicia indicative of the emergence of ulcers and/or other skin abnormalities at particular locations on the captured image. In another example, the CPU 115 is configured to detect for areas on the captured images including at least one of excess callous, blisters, moisture, and discolouration.

Other information and/or data relevant to the operation of the present systems and methods, such as a database 185, may also be stored on the memory 160. The database 185 may contain and/or maintain various data items and elements that are utilized throughout the various operations. It should be noted that although the database 185 is depicted as being configured locally to the device 100, in certain implementations the database 185 and/or various other data elements stored therein may be located remotely. Such elements may be located on a remote device or server—not shown, and connected to the device 100 through a network in a manner known to those skilled in the art, in order to be loaded into a processor and executed.

Further, the program code of the software modules 170 and one or more computer readable storage devices (such as the memory 160) form a computer program product that may be manufactured and/or distributed in accordance with the present disclosure, as is known to those of skill in the art.

The communication interface 165 is also operatively connected to the CPU 115 and may be any interface that enables communication between the device 100 and external devices, machines and/or elements. The communication interface 165 is configured for transmitting and/or receiving data. For example, the communication interface 165 may include but is not limited to a Bluetooth, WiFi; or cellular transceiver, a wireless module, a satellite communication transmitter/receiver, an optical port and/or any other such, interfaces for connecting the device 110 to external devices.

The user interface 150 is also operatively connected to the CPU 115. The user interface may comprise one or more input device(s) such as switch(es), button(s), key(s), or a touchscreen. The user interface 150 functions to allow the entry of data. The user interface 150 functions to facilitate the capture of commands from the user such as an on-off commands or settings related to operation of the above-described method.

A display 190 may also be operatively connected to the CPU 115. The display 190 may include a screen or any other such presentation device that enables the user to view various options, parameters, and results. The display 190 may be a digital display such as an LED display. The device 110 may be powered via a power supply 192. An alert mechanism 195 is provided for generating alerts. The alert mechanism 195 is operable to communicate the alert to a remote entity via a telecommunications network.

An exemplary operation of the device 100 is described with reference to the flowcharts 200, 300A and 300B. In block 202 a user steps onto the transparent panel 102. A strain gauge 169 which is operably coupled to the CPU 115 senses the weight load on the transparent panel 102, block 204. The strain gauge 169 is configured to determine when the user is in a stable position, block 206. A pre-measurement check is performed, block 208. The CPU 115 activates the LEDs 122, block 210. The temperature sensors 105 are activated to record the temperature of an area of skin on the sole of the foot 109 in contact with the transparent panel 102, block 212. In this exemplary embodiment, two image capture devices 107 are activated to capture an image of the sole of the individuals foot 109 as well as the temperature sensors 105 which record the temperature of the corresponding points on the sole of the foot 109, block 214. The temperature sensor 118 records the temperature of the transparent panel 102, block 216. In this example, the skin inspection device 110 may also function as a weighing scales to capture the individual's weight, block 218. The image data, weight data, reference temperature data, time stamp are recorded and sent to the CPU 115 for processing, step 220. It will be appreciated that it is not intended to limited the present teaching to the exemplary steps provided or to the order and sequence of the steps which may be modified as desired.

An exemplary data processing approach is described with reference to the flowchart 300A. The CPU 115 receives the image data, weight data, reference temperature data, time stamp, block 302. The image data is processed by the CPU 115, block 304. This processing may include the CPU 115 applying an algorithm that would scan the captured image and identify the location of the temperature sensors 105. The locations of the temperature sensors 105 in the captured image are linked to temperature data recorded by the sensors 105, block 306. The CPU 115 generates a temperature dataset based on the recorded temperature values of the sensors 105, block 308. The temperature dataset is stored in database 185. The reference temperature and offset algorithm are applied to the temperature dataset by the CPU 115, block 310. The modified temperature dataset is stored in a patient database, block 312. The image data, weight data, reference temperature and time stamp are also stored in the database, block 314. If it is determined that the temperature values in the temperature dataset indicate the formation of DFU an appropriate indicia is displayed on the display 190 alerting the individual of a potential ulceration, block 316. It will be appreciated that it is not intended to limited the present teaching to the exemplary steps provided or to the order and sequence of the steps which may be modified as desired. For example, the inclusion of the weight data may be optional in the data processing approach described above.

Figure 13A:
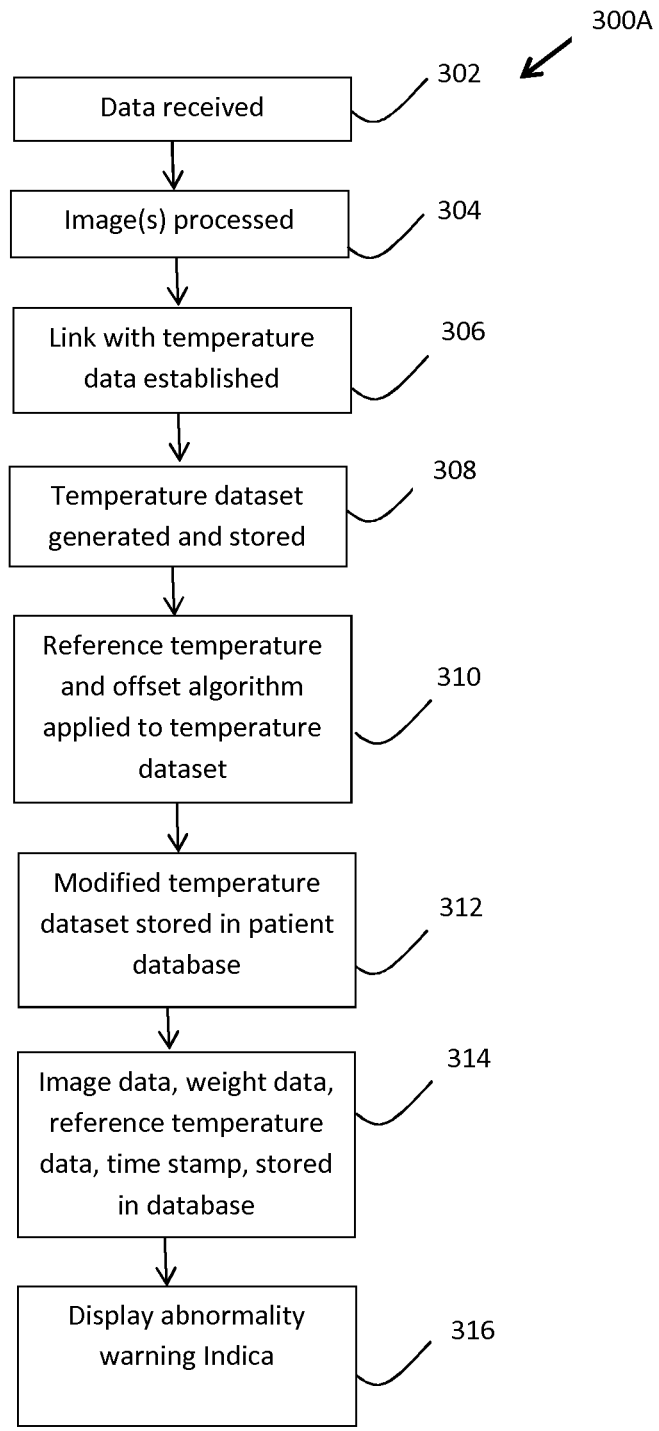
FIG. 13A is a flow chart detailing exemplary steps carried by a skin inspection device in accordance with the present teaching.
Figure 13B:
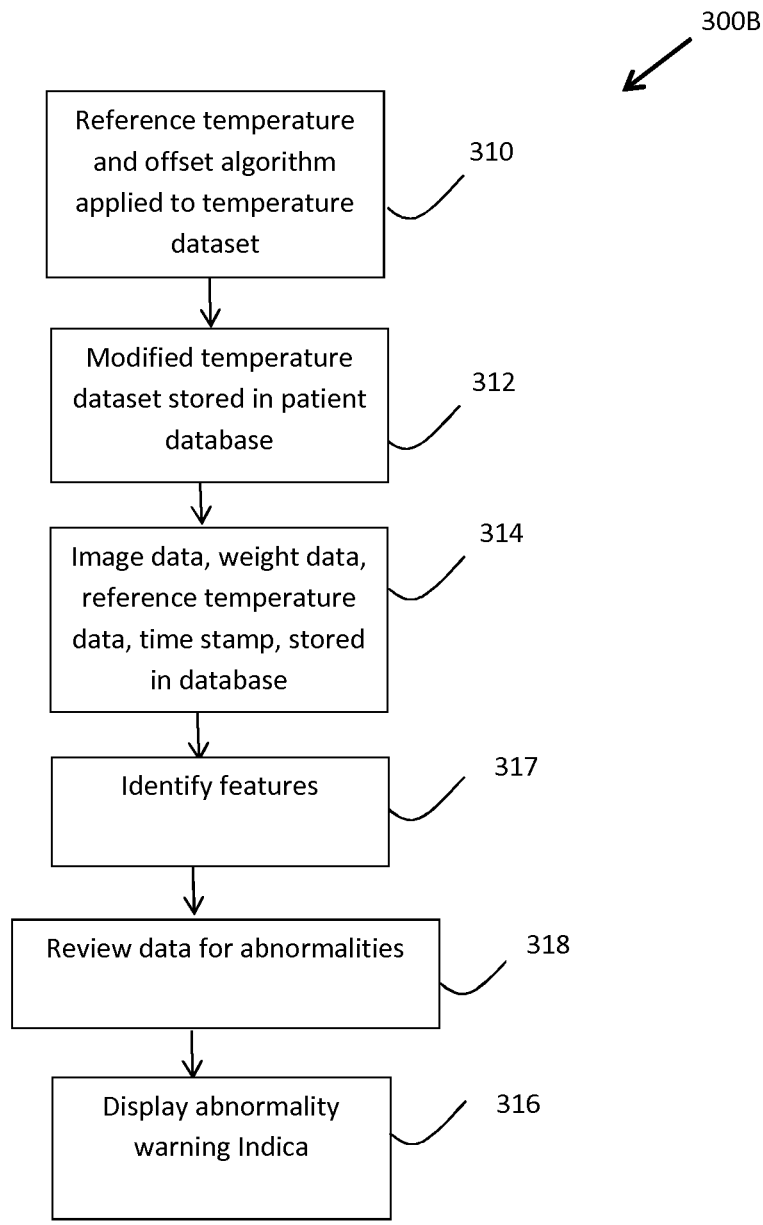
FIG. 13B is a flow chart detailing exemplary steps carried by a skin inspection device in accordance with the present teaching.

An alternative data processing approach is described with reference to the flow chart 300B. Blocks 310, 312, 314 and 316 correspond to the similarly labeled blocks in FIG. 13B. Blocks 317 and 318 describe an alternative approach. Features may be identified by various computer vision means well known to those skilled in the art, such as hue analysis, blob, corner, edge analysis and other such feature detection algorithms, block 317. Features may also be identified through comparison to a database of tagged features. A tagged dataset may also be used as a training set for a machine learning algorithm, for example using neural networks. Features may include the feet, including its size, shape, orientation etc. Other features which may be detected may include ulcers, toes, callus, discoloration, cuts, blisters, or the like.

The system may be configured to detect visual or thermal abnormalities, or a combination of both, block 318. Visual abnormalities may be detected by first identifying the feet within the image. The feet are then reviewed for abnormal features. Thermal abnormalities may be identified by using just the thermal data, or by combining the visual image with the thermal data. The location of the foot may be determined using the visual image. This is advantageous as there are occasions when the temperate of the feet is similar to ambient temperature, and hence it can be difficult to determine the location of the feet using thermal data alone. As such it can be difficult to perform comparisons between points on one foot and the other as it is difficult to determine which points to compare.

By linking the images of the feet with the temperature dataset it is possible to determine the temperature at any location on the foot. Abnormalities may be detected by comparing the temperature between like for like points on the feet (a contralateral comparison). Other methods of detecting abnormalities may include comparing the average, maximum, minimum temperature, or any other statistically generated number. Another method is to compare the data collected to previously collected data. In certain patients there may be a pre-existing temperature difference between contralateral sites, and in these instances it would be advantageous to compare the temperature to previously recorded temperatures. In another embodiment, a comparison of regional temperatures may be carried out, such as the forefoot, the heel, the hallux etc.

It is advantageous to review two different sensing modality datasets (thermal and visual) as it increases the level of information available to determine the presence of abnormalities. Some abnormalities may only be present in one of the datasets. It is advantageous as in gives four potential outcomes, whereas with a single sensing modality there are only two.

| Outcome | Thermal | Visual |
| --- | --- | --- |
| 1 | OK | OK |
| 2 | OK | Not OK |

| Outcome | Thermal | Visual |
|---|---|---|
| 3 | Not OK | OK |
| 4 | Not OK | Not OK |

The system may be configured to alter the alert based on the type of abnormalities detected. For example the indicia generated by a contralateral temperature increase without the presence of a visual abnormality may be different to the indicia generated if an active ulcer is detected.

Points in the image may be used to identify physical items such as toes, heel, arch, etc. The image may be digitised in order to generate a geometrical map of the foot. Different areas of the images may be classified based on characteristic. These classified areas may be used as reference point(s) when comparing both feet. The geometrical map may be used to identify a physical formation at a given coordinate. Thus the geometrical map allows accurate comparison to the same region on the other foot. This facilitates easy mapping data from each foot at similar points.

Figure 14A:
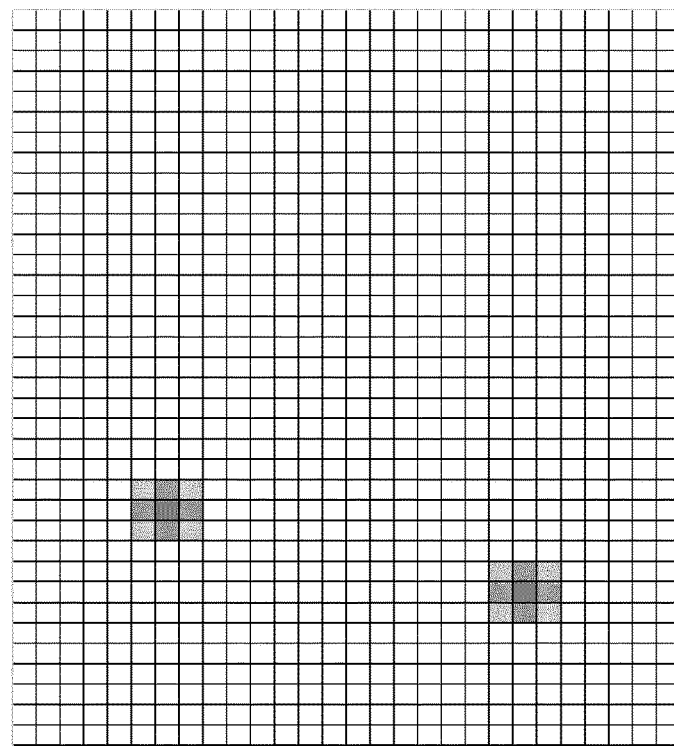
FIG. 14A is a visual representation using temperature data only.

Foot temperate is usually below body temperature. Often foot temperature can be similar temperature to ambient temperature. In such instances, it is not possible to determine where in a heat map corresponds to the foot. Hence it can be difficult to perform a contralateral temperature comparison. FIG. 14A provides an indication of a possible temperature data set which may be recorded using an array of temperature sensors 105. A significant portion of the foot is similar to ambient temperature, and hence it is not possible to distinguish from the temperature sensors 105. There are however two areas of increased temperature in the heat map. The primary mode of determining if a temperature is abnormal is to perform a contralateral comparison i.e. compare it to the same point on the other foot.

Figure 14B:
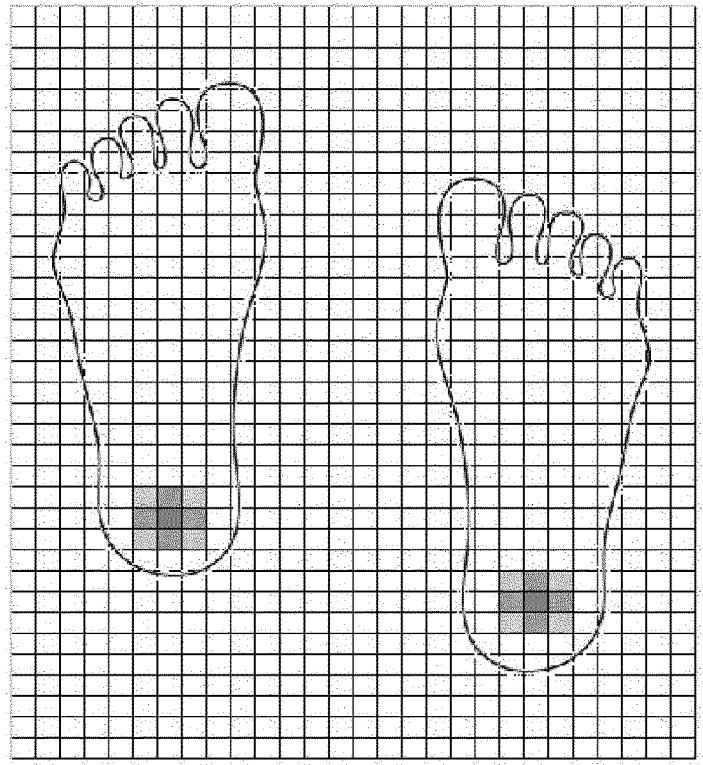
FIG. 14B is a visual representation combining temperature data and an image of a target.
Figure 14C:
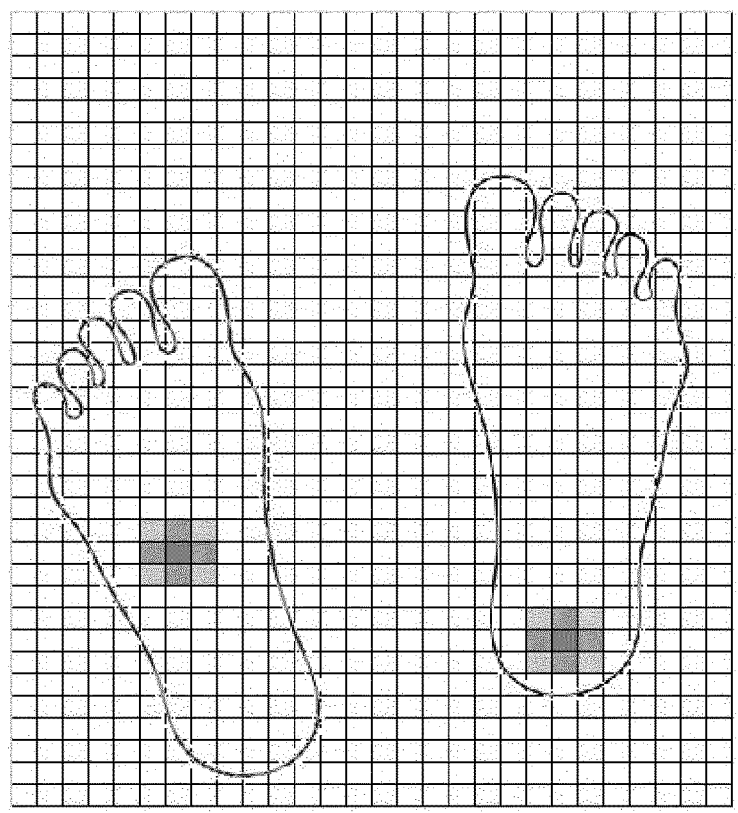
FIG. 14C is a visual representation combining temperature data and an image of a target.

FIGS. 14B and 14C indicate how the combining the datasets provides additional information which increases the usefulness of the temperature data. In FIG. 14A it is not possible to determine if the two areas of increased temperature corresponds to the same location on the feet (as demonstrated in FIG. 14B), or if they correspond to different locations (as demonstrated in FIG. 14C). The diagnosis is reversed from healthy to unhealthy based on this additional information. FIG. 14B combines temperature data with visual data and may be used to confirm that the hot spot sites correspond to same location on the foot. In a contralateral comparison, this would indicate that the temperatures are normal. FIG. 14C also combines temperature data with visual data and can be used to determine if the hotspots are at different locations on the feet. The visual image may be used to confirm that the hot spot sites correspond to different location on the feet. In a contralateral comparison, this would indicate that the temperatures are not normal.

Figure 15:
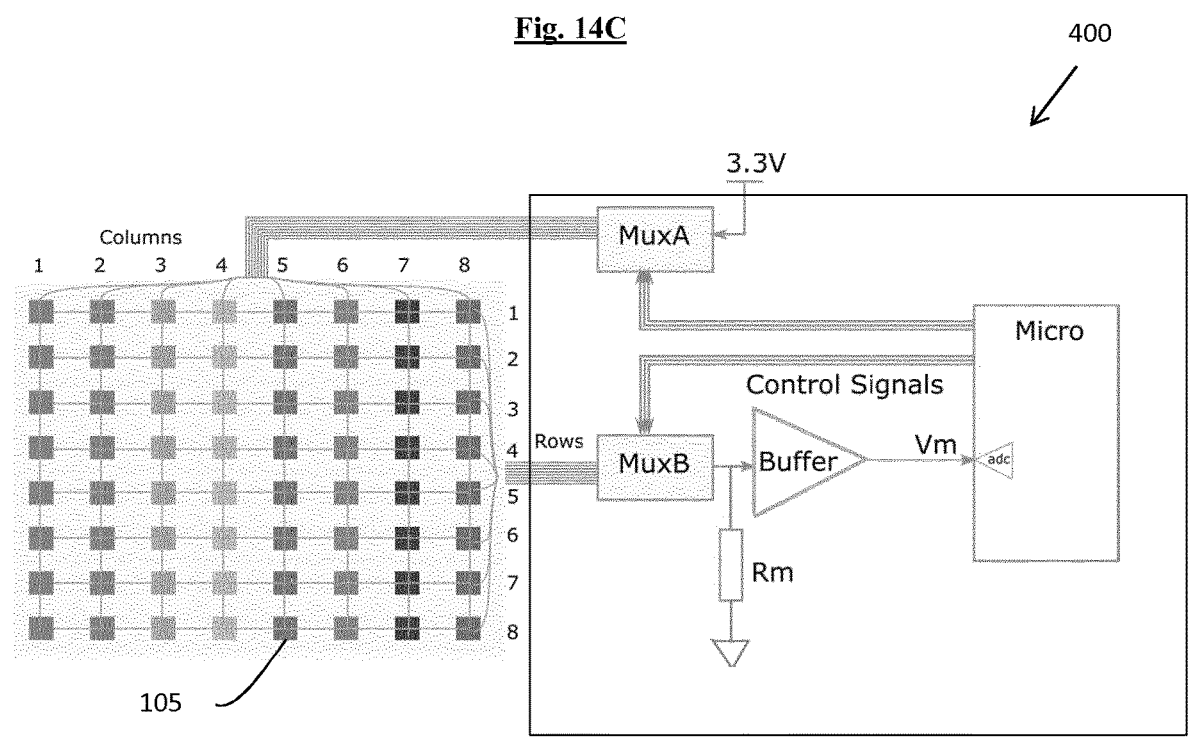
FIG. 15 illustrates an exemplary read-out circuit of a skin inspection device in accordance with the present teaching.
Figure 16:
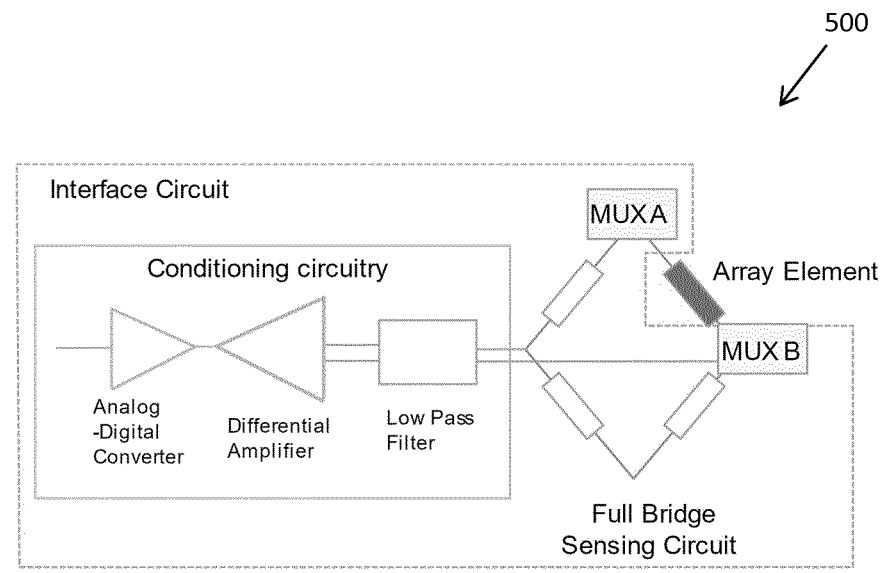
FIG. 16 illustrates another exemplary read-out circuit of a skin inspection device in accordance with the present teaching.

Referring now to FIG. 15 which illustrates an exemplary read-out circuit of a skin inspection device in accordance with the present teaching. The read-out circuit 400 is in communication with the array of temperature sensors 105 which is shown in a matrix configuration. Temperature sensing is achieved by reading a voltage. Each element of the array of temperature sensors 105 can be individually read using two switching multiplexers, one for row selection (MuxB) and one for column selection (MuxA). The read-out circuit 400 is configured as a half-bridge circuit. An alternative embodiment of a read out circuit 500 is that of a full-bridge circuit which is shown in FIG. 16.

The maximum read speed of a single array element is a function of the multiplexer switching speed, the Analog to Digital Converter read speed and signal switching noise due to parasitic capacitances and resistances. To minimise the noise and temperature dependency of the sensing system, conditioning circuitry may be used to filter out high frequency noise using a low pass filter, amplify the signal using a differential amplifier and perform an analog to digital conversion.

Figure 17:
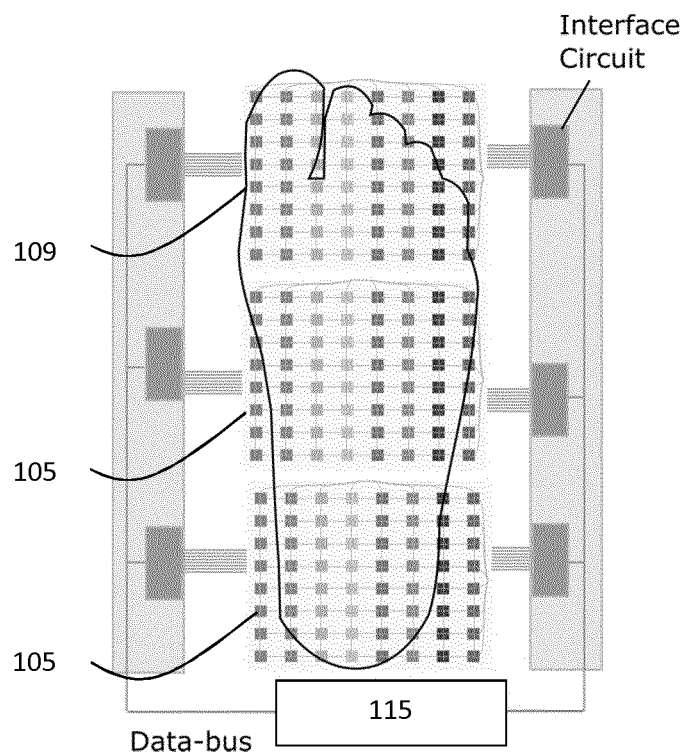
FIG. 17 illustrates exemplary details of a skin inspection device in accordance with the present teaching.

FIG. 17 illustrates exemplary read-out circuitry 400 located along the length of the foot 109 so that simultaneous sampling of the arrays of temperature sensors 105 can occur. This minimizes the overall scanning/inspection time reducing inconvenience for the user. The read-out circuitry is in communication with the CPU 115 for translating the data read from the sensors 105 into temperature values. The connection between the read-out circuitry 400, 500 and the CPU 115 may be a high speed digital bus such as I2C or SPI and the bus connections should be concealed from the field of view of the image capture device 107. The array of temperature sensors 105 are arranged in a grid with a row-column configuration. The temperature sensors 105 are spaced such that optical pathways exist between the temperature sensors 105 allowing for an image of the sole of the foot 109 in contact with the temperature sensors 105 to be captured. An optical pathway may also be defined by a zone between two or more adjacent temperature sensors 105. The temperature sensors 105 are addressable through coordinates and the coordinates of the sensors 105 may correspond to one or more pixels in the captured image. The CPU 115 is operable to map a graphical region of the sole of the foot 109 under inspection to coordinates of the temperature sensors 105.

It will be appreciated by the person of skill in the art that various modifications may be made to the above described embodiments without departing from the scope of the present invention. In this way it will be understood that the teaching is to be limited only insofar as is deemed necessary in the light of the appended claims. In the exemplary arrangement; multiple image capture devices are illustrated, however, it will be appreciated that a single image capture device may be used.

It will be appreciated by the person of skill in the art that various modifications may be made to the above described embodiments without departing from the scope of the present invention. In this way it will be understood that the teaching is to be limited only insofar as is deemed necessary in the light of the appended claims. In an exemplary embodiment; the skin inspection device 100 may be incorporated into a weighing scales which would have a means for calculating the weight of an individual.

Similarly the words comprises/comprising when used in the specification are used to specify the presence of stated formations, integers, steps or components but do not preclude the presence or addition of one or more additional formations, integers, steps, components or groups thereof.

The invention claimed is:

1. A skin inspection device for identifying skin abnormalities; the skin inspection device comprising:
   a transparent panel having an inspection area;
   an array of contact temperature sensors provided on the transparent panel to record temperature data of an area of skin of a target located in the inspection area,
   wherein the array of the contact temperature sensors are configured to be in contact with the area of the skin;

one or more cameras for capturing an image of the array of contact temperature sensors and of the area of the skin;
a processor operably coupled to the one or more cameras and the array of contact temperature sensors for controlling operations of:
combining the recorded temperature data with image data of the image to generate a data set,
analyzing the dataset to identify the skin abnormalities; and
generating indicia indicative of an emergence of ulcers and/or other skin abnormalities,
wherein the array of the contact temperature sensors are spaced such that optical pathways exist between two or more adjacent contact temperature sensors of the array of the contact temperature sensors through the transparent panel,
wherein the contact temperature sensors of the array of the contact temperature sensors occlude light transmission through the transparent panel to the skin, allowing the one or more cameras to capture the image of the array of contact temperature sensors and of the area of skin of the target located in the inspection area,
wherein the area of the skin comprises a first area of the skin visible to the one or more cameras through the transparent panel and a second area of the skin contacted by the contact temperature sensors,
wherein the first area is defined by the optical pathways,
wherein the first area and the second area are inversely proportional to each other,
wherein the contact temperature sensors are addressable through coordinates which correspond to one or more pixels in the image comprising the first area and the second area, and
wherein the processor is configured to associate regions of the image comprising the first area and the second area to the coordinates of the array of contact temperature sensors.

2. The skin inspection device as claimed in claim 1, further comprising a strain gauge operable for detecting a weight bearing load on the transparent panel.

3. The skin inspection device as claimed in claim 2, wherein the processor is configured to activate the one or more cameras in response to the strain gauge detecting the weight bearing load.

4. The skin inspection device as claimed in claim 1, further comprising a housing on which the transparent panel is mounted.

5. The skin inspection device as claimed in claim 4, wherein the housing accommodates the processor and the one or more cameras therein.

6. The skin inspection device as claimed in claim 1, wherein the transparent panel provides a foot plate to support the weight of an adult human.

7. The skin inspection device as claimed in claim 1, wherein the transparent panel is rigid.

8. The skin inspection device as claimed in claim 1, wherein the transparent panel is of a flexible material operable to conform to the shape of a sole of a foot when stepped on by an individual.

9. The skin inspection device as claimed in claim 1, wherein the array of contact temperature sensors are provided on an upper surface of the transparent panel.

10. The skin inspection device as claimed in claim 1, wherein the array of contact temperature sensors are mounted on the transparent panel.

11. The skin inspection device as claimed in claim 1, wherein the processor is configured to process the image captured of the array of contact temperature sensors and of the area of skin by the one or more cameras, the processor determining the recorded temperature data of the area of skin of the target at multiple discrete locations based on the image captured of the array of contact temperature sensors and of the area of skin by the one or more cameras.

12. The skin inspection device as claimed in claim 11, wherein the processor is configured to generate a temperature dataset based on the recorded temperature data of the area of skin of the target at the multiple discrete locations.

13. The skin inspection device as claimed in claim 12, wherein the temperature dataset includes the recorded temperatures data by the array of contact temperature sensors.

14. The skin inspection device as claimed in claim 12, wherein the processor is configured to associate temperature values in the temperature dataset with the multiple discrete locations on the image of the array of contact temperature sensors and of the area of skin of the target.

15. The skin inspection device as claimed in claim 12, wherein the processor is configured to perform analysis on the temperature dataset and the image captured of the array of contact temperature sensors and of the area of skin.

16. The skin inspection device as claimed in claim 15, wherein the analysis compares the recorded temperature data from the array of contact temperature sensors assigned to similar points of the image captured of the array of contact temperature sensors and of the area of skin.

17. The skin inspection device as claimed in claim 12, wherein the processor is operable to generate the indicia indicative of the emergence of the skin abnormalities at the multiple discrete locations on the image captured of the array of contact temperature sensors and of the area of skin.

18. The skin inspection device as claimed in claim 17, wherein the indicia comprises the temperature dataset.

19. The skin inspection device as claimed in claim 1, wherein the processor is configured to detect for areas on the captured images including at least one of callous, blisters, moisture, and discolouration.

20. The skin inspection device as claimed in claim 1, further comprising an alert mechanism for generating an alert.

21. The skin inspection device as claimed in claim 20, wherein the alert mechanism is operable to communicate the alert to a remote entity via a telecommunications network.

22. The skin inspection device as claimed in claim 1, wherein the one or more cameras are configured to be triggered to capture the image of the array of contact temperature sensors and of the area of skin in response to an input.

23. The skin inspection device as claimed in claim 1, wherein the one or more cameras are configured to be triggered to capture the image of the array of contact temperature sensors and of the area of skin in response to a foot being placed on the inspection area.

24. The skin inspection device as claimed in claim 1, wherein the array of contact temperature sensors are spaced approximately 1 per 1 $cm^2$.

25. The skin inspection device as claimed in claim 1, wherein a spatial resolution of the array of contact temperature sensors is in a range of 0.5 per $cm^2$ to 6 per $cm^2$.

26. The skin inspection device as claimed in claim 1, wherein each contact temperature sensor of the array of contact temperature sensors has a diameter in range of 0.1 mm to 4 mm.

27. The skin inspection device as claimed in claim 1, wherein the transparent panel is comprised of glass; or a composite material; or polycarbonate or other plastics material.

28. The skin inspection device as claimed in claim 1, further comprising a light source.

29. The skin inspection device as claimed in claim 28, wherein the light source comprises one or more Light-Emitting Diodes (LEDs).

30. The skin inspection device as claimed in claim 1, further comprising a light filter to alter light intensity entering a field of view of the one or more cameras.

31. The skin inspection device as claimed in claim 30, wherein, a calibration target is located in the area of the overlap in the field of view.

32. The skin inspection device as claimed in claim 1 further comprising one or more diffusion films for reducing glare on the transparent panel.

33. The skin inspection device as claimed in claim 1, wherein the transparent panel has an opaque layer with transparent foot shaped sections.

34. The skin inspection device as claimed in claim 1, wherein the one or more cameras includes two cameras, and wherein the two cameras are provided with an area of overlap in the field of view.

35. The skin inspection device as claimed in claim 1, further comprising a light sensor within a field of view of one of the one or more cameras.

36. The skin inspection device as claimed in claim 35, wherein an output from the light sensor is used by the processor to modify operational settings of one of the one or more cameras.

37. The skin inspection device as claimed in claim 35, wherein the output from the light sensor is used as an input by a post processing algorithm to eliminate effects of ambient light.

38. The skin inspection device as claimed in claim 1, further comprising a heat sensor for sensing a temperature of the transparent panel.

39. The skin inspection device as claimed in claim 1, further comprising one or more baffles configured to block at least a portion of glare-causing rays of light.

40. The skin inspection device as claimed in claim 39, wherein the one or more baffles are selectively adjustable.

41. The skin inspection device as claimed in claim 40, wherein at least one of a dimension, configuration, orientation or location of the one or more baffles are selectively adjustable.

* * * * *